(12) United States Patent
Gaumer et al.

(10) Patent No.: US 6,852,340 B1
(45) Date of Patent: Feb. 8, 2005

(54) BIOCIDE COMPOSITION CONTAINING PROPIONIC ACID AND IODINE COMPOUNDS

(75) Inventors: Gary E. Gaumer, Chico, CA (US); Bruce A. Spielholz, Alpharetta, GA (US)

(73) Assignee: Preserve International, Chico, CA (US)

( * ) Notice: Subject to any disclaimer, the term of this patent is extended or adjusted under 35 U.S.C. 154(b) by 0 days.

(21) Appl. No.: 09/532,140

(22) Filed: Mar. 21, 2000

(51) Int. Cl.$^7$ .......................... A61K 33/36; A01N 59/22
(52) U.S. Cl. ........................ 424/667; 424/668; 424/669
(58) Field of Search ............................... 424/667, 668, 424/669, 600

(56) References Cited

U.S. PATENT DOCUMENTS 5,462,714 A * 10/1995 Talwalker et al. ............ 422/37
6,183,794 B1 * 2/2001 Kaesler et al. ............... 426/335

FOREIGN PATENT DOCUMENTS

WO          8900006    * 1/1989

* cited by examiner

*Primary Examiner*—Alton Pryor
(74) *Attorney, Agent, or Firm*—Willie Krawitz

(57) ABSTRACT

A biodegradable composition having long term phase and composition stability, and a method for producing both short and long period biocide activity, is used for disinfecting animal husbandry surfaces, in the medical and food industry, and the like. The composition contains propionic acid for pH control, and preferably iodine or an iodine containing compound. The propionic acid combines with ambient ammonia, or ammonia containing compounds arising from fermenting litter and manure to form ammonium propionate, which in turn inhibits or prevents microorganism formation, including mold formation. A surfactant which complexes with the iodine may also be used for spraying onto surfaces, and is effective in the presence of a high organic challenge and hard water.

9 Claims, No Drawings

BIOCIDE COMPOSITION CONTAINING PROPIONIC ACID AND IODINE COMPOUNDS

BACKGROUND OF INVENTION

This invention relates to a new and improved, biodegradable biocide-composition having mold inhibiting or prevention activity and which provides both long and short term activity in animal husbandry use, and for the medical and food industry, and the like. The present biocide composition retains activity in the presence of significant amounts of organic matter and hard water and provides an activity having a short inception time, and for a significant period thereafter; also, the shelf life of the present composition has a significant shelf life.

Biocides for use particularly in animal husbandry locations, and the like, require a suitable activity against a wide variety of microorganisms such as bacteria, molds, spores and viruses, and in the presence of significant amounts of organic matter and using hard water. Additionally, this activity should have a short inception period such as ten minutes, and be effective for a significant period of time thereafter, such as for at least five hours. Also, these biocides should be capable of being used not only for spraying onto surfaces, but also to inhibit or remove airborne contamination, particularly in poultry houses, where dust and airborne particles may carry many types of diseases. Also, biocides generally should be biodegradable, and possess a long shelf life yielding phase and composition stability such as about twelve to eighteen months.

Many biocides are well known, and publications of these types are found in U.S. Pat. Nos. 3,028, 299; 3,150,096; 3,367,877; 3,438,905; 3,644,650; 3,697,651; 3,728,449; 4,059,615; 4,107,312; 4,226,866; 4,923,899; 4,957,912; 4,983,635; 5,030,659; 5,124,359; 5,284,675; 5,344,838; 5,338,746; 5,368,868; 5,391,379; 5,419,908; 5,500,138; 5,668,102; 5,891,922 and, French Patent 2,622,397.

U.S. Pat. Nos. 5,338,748 and 5,344,838 both disclose using arsenic, chromium, cyanides, lead and selenium in the intended compounds, which would make them totally unsuitable for animal husbandry purposes. Hence, it is considered these patents do not describe a combination of the desired properties of a biocide composition for the intended usage. U.S. Pat. Nos. 3,728,449 and 5,368,868 describe the use of iodine, propylene glycol and a block copolymer of polyoxyethylene and polyoxypropylene as a germicidal composition, but they are used as a bovine teat dip, and are too mild as a biocide in an animal husbandry environment.

THE INVENTION

According to the invention, a biocide composition is provided comprising, propionic acid and iodine (I or I$^-$) or an iodine containing compound such as hydriodic acid (HI$^-$) or equivalent such as NaI, KI, CaI$_2$, etc., and iodophors. HI$^-$ is one of the preferred iodine containing compounds since it promotes phase and composition stability, thereby adding about twelve to eighteen months to the shelf life at ambient temperature.

The propionic acid functions to control pH, and to combine with ambient NH$_3$ to form ammonium propionate, thereby producing residual biocidal activity, which inhibits or prevents microorganism formation, including mold formation. The composition may have efficacy as a bovine teat dip, either as ammonium propionate and/or as propionic acid with iodine. Other propionates such as butyrates, valerates and isovalerates and their salts (e.g., Ca, Na, K, etc.), esters, etc., may be used.

Air spraying with minimal or no water, will neutralize or minimize airborne contamination such as dust, organic material and particulates which may harbor airborne diseases. Used in liquid form for spraying onto animal husbandry surfaces, instead of airborne spraying, the iodine containing propionic acid may be mixed with a surfactant to complex or stabilize the iodine.

Added materials which may be employed include: water dilution; dust inhibitors such as propylene glycol; and, additional acidifying and buffering agents such as citric, lactic, sorbic, maleic and fumaric acids, and their salts, esters and mixtures thereof. Other stronger acidifying agents such as phosphoric and/or sulfuric acid, and the like may be used for imparting a suitable pH range to the composition of between about –1 to 5, while a narrower, preferred pH range is approximately –1 to 3:

When used to spray surfaces, a suitable surfactant carrier is a block copolymer of propylene oxide and ethylene oxide such as sold by BASF Corp. under the registered trade marks of PLURONIC® and TETRONIC®; these copolymers are nonionic, liquid surfactants with an HLB range of about 1.0–7.0. Other liquid, anionic, biodegradable surfactants having iodine complexing capability in the same or similar HLB range may be employed, and are found in "McCutcheon's Emulsifiers & Detergents", Vol. 1: 1989 to 1999 (incorporated herein, by reference).

Suitable surfactants are also described in U.S. Pat. Nos. 5;534,266 and 5,720,984 (incorporated herein by reference), the latter patent disclosing a non-ionic, laureth (11–16) carboxylic acid surfactant teat dip and hand foam which is highly suitable as the surfactant for use in this invention. Additional publications concerning bovine teat dip formulations are described in U.S. Pat. Nos. 4,012,504; 4,049,830; 4,759,931; 5,529,770; 5,641,498; 5,368,868; 5,616,348; and, 5,651,977. Polyethenoxy detergents and I, are disclosed in an article by Benjamin Carroll in the Journal of Bacteriology, 69: 413–417, (1955). A PVP surfactant for a teat dip is also suitable, and also one sold by Norman Fox & Co. under the trade name of NORFOX N-P9, and listed in "McCutcheon's Emulsifiers and Detergents 1989", specifically for use with iodophors.

Other types of teat dips are sold as Klenzade™ Teat Guard containing a nonyl phenoxypolyethoxy ethanol surfactant and titratable iodine. U.S. Pat. No. 5,616,348 (supra) discloses a polyethoxylated polyoxypropylene block copolymer (Poloxamer) and iodine, but which does not employ propionic acid.

U.S. Pat. No. 5,967,202 to Ecolab, Inc. describes the manufacture of bovine teat dips by feeding components from an automatic dispensing apparatus to a milking station. The Ecolab, patent lists a wide variety of medicaments and surfactants which may be used in the manufacture of bovine teat dips, and are incorporated by reference herewith. The Ecolab patent also describes the use of defoaming agents for processing purposes (col. 19), which is distinct from a foam bovine teat dip.

A broad concentrate composition comprises: iodine: at least about 0.1%; hydriodic acid: at least about 0.01%; propionic acid: at least about 10%; phosphoric acid and/or sulfuric acid, and the like: sufficient to obtain a pH of about –2 to 3; a buffer: at least about 1%; and, a polyhydric alcohol such as propylene glycol, glycerol, mannitol, sorbitol, butylene glycols, and the like: at least about 5%, all parts by weight.

A narrower, preferred composition comprises: iodine: about 0.1%–5%; hydriodic acid: about 0.01%–2%; propionic acid, and the like: about 10%–75%; phosphoric acid, and/or sulfuric acid, and the like: sufficient to obtain a pH of about −2 to 3; a buffer: at least about 1%; and, propylene glycol, and the like: about 5%–30%, all parts by weight.

A coverage of from 2,500–30,000 square feet of surface preferably uses 5–60 gallons of concentrate for 100–1,200 gallons of potable water (1:20). and employs an inception contact time of about ten minutes and a contact period of preferably about five hours. The composition is usually dispensed using a coarse spray for maximum contact and penetration, or by atomization into ambient air so as to neutralize dust and organic material, etc. which may harbor airborne contamination; and, by fumigation. Typically, the product is used on, but not limited to dirt floors, new and used litter, rice hulls, oyster shells, concrete floors, and any other substrate material where animal husbandry is conducted.

Prior to use, all poultry, animals, feed and portable equipment may he removed from the premises to be treated to assure adequate surface coverage, and all water troughs and feed racks are emptied. Alternatively, since the present composition employs feed grade components, it is not required to remove animals during use, and the premises may be treated in the presence of animals as an ongoing remedy for retarding $NH_3$ build-up, and/or microorganism development and growth. Surfaces such as floors, ceilings, walls, walkways, etc., of an animal husbandry facility which may include poultry houses, cattle barns, swine facilities, cattle facilities, zoos, and other animal raising facilities are washed and disinfected with a suitable detergent and disinfectant, and allowed to dry.

The biocide solution of this invention is then sprayed downwardly from the curtains to the floor and thoroughly wetting the desired area to be disinfected. The solution should be allowed to contact the treated surface for a period for at least ten minutes, and the buildings, coops and other closed spaces under treatment should be thoroughly ventilated. Shoe baths containing one inch of biocide solution should be placed at the entrance to a facility and replaced daily.

In general, viruses, bacteria, vegetative spores, protozoa and viruses are sterilized by the composition of this invention, and typical organisms which can be neutralized by the composition of this invention in the presence of 50% organic soil and 1,000 pm hard water, at dilutions of 1:20, include: vegetative clostridium perfigens, which is known to cause gangrenous dermatitis in poultry. Also included in the above test scheme were tests performed in conformance with A.T.C.C., Fifteenth Edition on the following: staphylococcus aureus A.T.C.C. 6538; salmonella choleraesuis 10708; pseudomonas areuginosa A.T.C.C. 15442; salmonella pullorum A.T.C.C. 9184; salmonella enteritidis A.T.C.C. 13076; clostridium perfigens A.T.C.C. 13124 (vegetative cells); salmonella typhimurium A.T.C.C. 14028; eacherichia coli A.T.C.C. 25922; pasteurellae multocida A.T.C.C. 43137; aspergillus fumigatus A.T.C.C. 36807; aspergillus glaucus A.T.C.C. 14567; and, infectious bursal disease virus (GUMBORO).

In addition to the above organisms which are neutralized by the biocide composition of this invention, harmful odors in an animal facility are neutralized; this prevents molds and other harmful microorganisms from becoming airborne.

Moreover, sterilization is obtained even in the presence of high levels of organic matter including, but not limited to dirt floors, manure and litter. Presently, disinfectants are limited to functioning well in the presence of only about five to ten percent of organic matter, but the composition of this invention functions in the presence of about 50% organic matter and at high levels of water hardness, such as up to about 1,000 ppm.

The composition of this invention provides an inexpensive and reliable biocide for sterilizing animal husbandry surfaces which is effective in high levels of organic material, for effective periods of contact time, and which retains potency for about twelve to eighteen months at ambient temperatures. As mentioned, it is possible that the composition of this invention may also have efficacy as a bovine teat dip.

What is claimed is:

1. A biocide concentrate composition for use in hard water, and in the presence of organic matter, consisting of:

a.) a surfactant for complexing or stabilizing iodine;

b.) a biocidal amount of at least about 0.1% iodine complexed by the surfactant and by at least about 0.01% hydriodic acid complexed by the surfactant;

c.) at least about 10% propionic acid, or propionates, or their salts and esters with ambient $NH_3$ from fermenting litter and manure to form ammonium propionate;

d.) acidifiers to adjust the composition pH to within the acid range of about −2 to 3;

e.) at least about 5% of propylene glycol; and, f.) at least about 1% of a buffer, all parts by weight.

2. The composition of claim 1, in which the surfactant is a polyoxyethylene polyoxypropylene block copolymer.

3. The composition of claim 1, in which the surfactant is selected from the group consisting of non-ionic laureth (11–16) carboxylic acid; polyvinyl pyrrolidone nonyl phenoxypolyethoxy ethanol; polyethenoxy; and, polyethoxylated polyoxypropylene block copolymer.

4. The composition of claim 1, in which the buffer is an acid selected from the group consisting of citric acid, sorbic acid, maleic acid, fumaric acid and their salts and esters, and mixtures thereof, and wherein water is present as a diluent in the composition.

5. A method for reducing or eliminating biocides from surfaces for animal husbandry, animal feed and food processing operations or from ambient air therein in the presence of hard water, consisting of: applying to the said surfaces a solution containing a surfactant, a biocidal amount of at least about 0.1% iodine, at least about 0.01% hydriodic acid, at least about 10% of propionic acid, or propionates, or their salts and esters for pH control, ambient $NH_3$ or ammonia containing compounds arising from fermenting litter and manure to form ammonium propionate, at least about 1% of a buffer, at least about 5% of propylene glycol and acidifiers to adjust the composition pH to within about −2 to 3, all parts by weight.

6. The method of claim 5, in which the surfactant comprises a polyoxyethylene polyoxypropylene block copolymer with an HLB of about 1.0–7.0.

7. The method of claim 5, in which the surfactant is selected from the group consisting of polyetheneoxy; non-ionic, laureth (11–16) carboxylic acid; polyvinyl pyrrolidone nonyl phenoxypolyethoxy ethanol; and, polyethoxylated polyoxypropylene block copolymer.

8. The method of claim 5, for use as a bovine teat dip.

9. A method for reducing or eliminating biocides from surfaces or ambient air in husbandry, animal feed and food processing operations in the presence of hard water, consisting of: applying to the said surfaces or ambient air a solution containing a surfactant, or by atomizing or fumigation into the ambient air, a biocidal amount of: up to 5% iodine; at least about 0.01%–2% hydriodic acid; about 10%–75% propionic acid or propionates, or their salts and ester; an acidifier acifficient to obtain a pH of about −2 to 3; about 1%–10% buffer; and, bout 5%–30% propylene glycol, all parts by weigh for combining with ambient $NH_3$ or ammonia containing compounds to form ammonium propionate, the buffer being selected from the class consisting of citric acid, lactic acid, maleic acid, fumaric acid, sorbic acid their salts and mixtures thereof, and water as a diluent.

* * * * *